(12) United States Patent
Del Portillo Obando et al.

(10) Patent No.: US 8,790,661 B2
(45) Date of Patent: Jul. 29, 2014

(54) **EXOSOMES DERIVED FROM RETICULOCYTES INFECTED WITH *PLASMODIUM* SP., METHOD FOR OBTAINING THEM AND USES THEREOF**

(75) Inventors: Antonio Hernando Del Portillo Obando, Barcelona (ES); Lorena Martin Jaular, Barcelona (ES); Carmen Maria Del Fernandez Becerra, Barcelona (ES)

(73) Assignees: Centre de Recerca en Salut Internacional de Barcelona, Barcelona (ES); Fundacio Cellex, Barcelona (ES); Hospital Clinic I Provincial de Barcelona, Barcelona (ES); Institucio Catalana de Recerca I Estudis Avancats, Barcelona (ES)

( * ) Notice: Subject to any disclaimer, the term of this patent is extended or adjusted under 35 U.S.C. 154(b) by 0 days.

(21) Appl. No.: 13/519,527

(22) PCT Filed: Dec. 28, 2010

(86) PCT No.: PCT/EP2010/070800
§ 371 (c)(1),
(2), (4) Date: Aug. 17, 2012

(87) PCT Pub. No.: WO2011/080271
PCT Pub. Date: Jul. 7, 2011

(65) Prior Publication Data
US 2012/0321676 A1 Dec. 20, 2012

(30) Foreign Application Priority Data
Dec. 28, 2009 (ES) .................................. 200931275

(51) Int. Cl.
*A61K 39/015* (2006.01)
*C07K 14/445* (2006.01)

(52) U.S. Cl.
USPC .................. 424/268.1; 424/184.1; 424/190.1; 530/350

(58) Field of Classification Search
CPC ..... A61K 38/00; A61K 39/00; C07K 14/415; C07K 14/445; C07K 14/715; C12N 1/36; C12N 9/6408
See application file for complete search history.

(56) References Cited

PUBLICATIONS

Houghten et al. (Vaccines, 1986, Edited by Fred Brown: Cold Spring Harbor Laboratory).*
Bhatnagar et al Blood. Nov. 1, 2007 ; 110(9): 3234-3244.*
Elandallouss et al 2002, Malaria Journal 1:6, pp. 1-7.*
Beauvillain, Céline et al., "Exosomes are an effective vaccine against congenital toxoplasmosis in mice," Vaccine 27 (2009) 1750-1757.
Engwerda, Christian R. et al., "The importance of the spleen in malaria," TRENDS in Parasitology vol. 21 No. 2 (Feb. 2005) 75-80.
European Patent Application EP 1 523 990 A1 (Institut National De La Sante et de La Recherche Medicale (Inserm) [FR]), published Apr. 20, 2005.
European Patent Application EP 0 841 945 B1 (Rijksuniversiteit te Leiden [NL]), published Mar. 8, 2006.
PCT International Publication No. WO 05/070418 A1 (M N L Pharma Limited), published Aug. 4, 2005.
PCT International Publication No. WO 08/092153 A2 (University of Louisville Research Foundation, Inc.), published Jul. 31, 2008.
Carlton, JM et al., "Comparative genomics of the neglected human malaria parasite *Plasmodium vivax*", Nature, (2008); vol. 455, pp 757-763.
Del Portillo, HA et el., "A superfamily of variant genes encoded in the subtelomeric region of *Plasmodium vivax*", Nature, (2001); vol. 410, pp. 839-842.
Elias JE and Gygi SP, "Target-decoy search strategy for increased confidence in large-scale protein identifications by mass spectrometry", Nat Methods, (2007), vol. 4, No. 3, pp. 207-214.
Esposito et al., "Intraertyhrocytic Administration of a Synthetic Plasmodium Antigen Elicits Antibody Response in Mice, Without Carrier Molecules or Adjuvants," Int'l J. Parasitology, vol. 20, No. 8, Dec. 1, 1990, pp. 1109-1111.
Fernandez-Becerra et al., "*Plasmodium vivax* and the importance of the subtelomeric multigene *vir* superfamily," Trends in Parasitology, vol. 25, No. 1, Jan. 1, 2009, pp. 44-51.
Jurado, JD, "Complement inactivating proteins and intraspecies venom variation in *Crotalus oreganus heileri*", Toxicon (2007), vol. 49, pp. 339-350.
Li Xiaobo et al., "Nanovesicular vaccines: exosomes," Arch. Immunol. Ther. Exp., vol. 53, No. 4, 2005, pp. 329-335.
Ribaut, C. et al., "Concentration and purification by magnetic separation of the erythrocytic stages of all human *Plasmodium* species", Malaria Journal (2008), vol. 7 No. 45.
Schorey JS and Bhatnagar S., Exosome Function: From Tumor Immunology to Pathogen Biology, Traffic (2008) vol. 9, pp. 871-881.
Tonkin, CJ et al., "Localization of organellar proteins in *Plasmodium falciparum* using a novel set of tranfection vectors and a new immunofluorscence fixation method", Molecular & Biochmecal Parasitology (2004), vol. 137, pp. 13-21.
Viaud, S. et al., "Exomomes for the Treatment of Human Malignancies", Horm Matab Res (2008), vol. 40, pp. 82-88.
PCT International Search Report issued on Jun. 22, 2011 connection with International Application No. PCT/EP2010/070800.
Written Opinion of the International Searching Authority issued on Jun. 22, 2011 in connection with International Application No. PCT/EP2010/070800.

\* cited by examiner

*Primary Examiner* — Padma V Baskar
(74) *Attorney, Agent, or Firm* — Gary J. Gershik; Cooper & Dunham LLP

(57) ABSTRACT

The present invention belongs to the field of vaccines for the prevention and prophylaxis against malaria, more specifically it relates to exosomes isolated from reticulocytes infected with *Plasmodium* sp., to methods for obtaining them and to the use thereof for the prevention and prophylaxis against malaria as well as to its use for the discovery and identification of novel *Plasmodium* antigens. The invention also refers to artificial exosomes comprising *Plasmodium* sp. antigens. Finally, the invention refers to specific antigens discovered by means of the exosomes obtained from reticulocytes infected with *Plasmodium* sp.

4 Claims, 15 Drawing Sheets

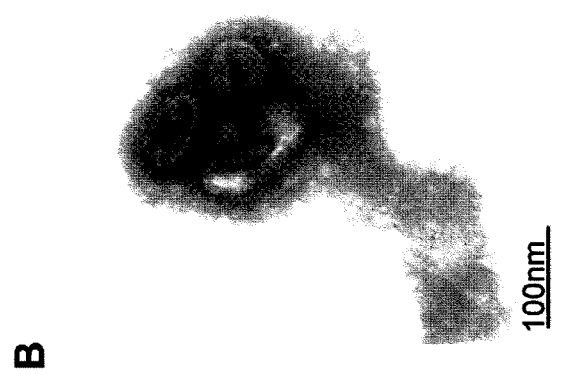
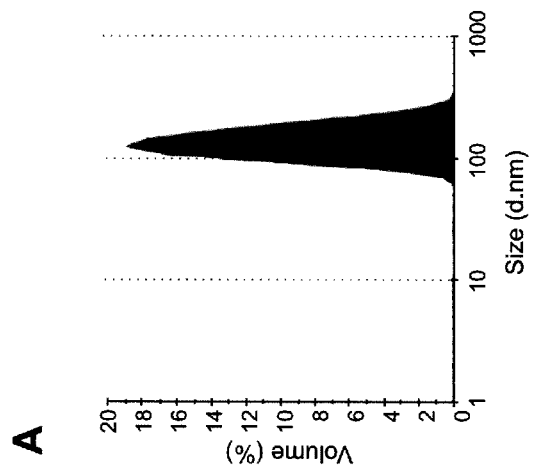
FIG. 1

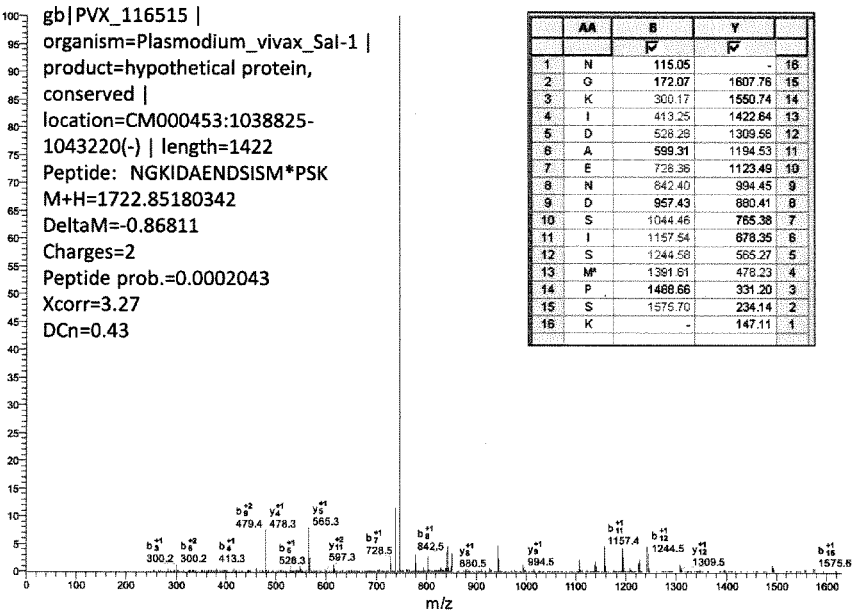
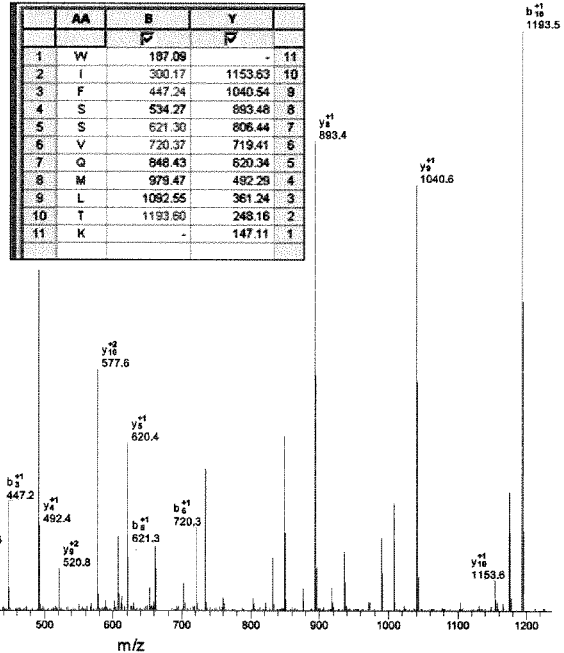
FIG. 8A

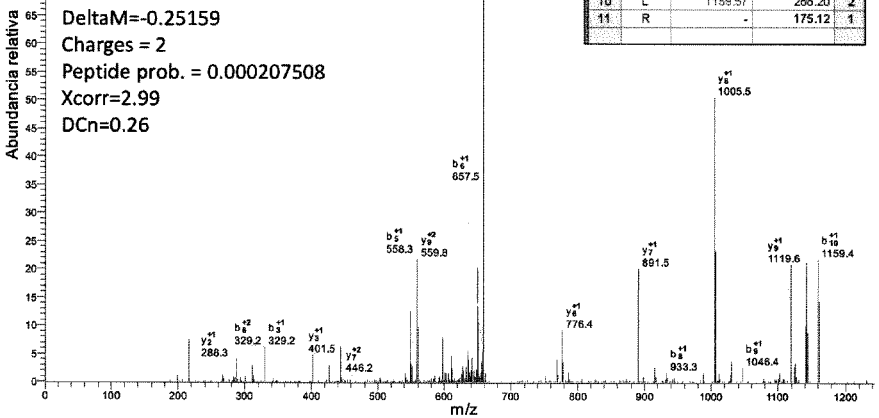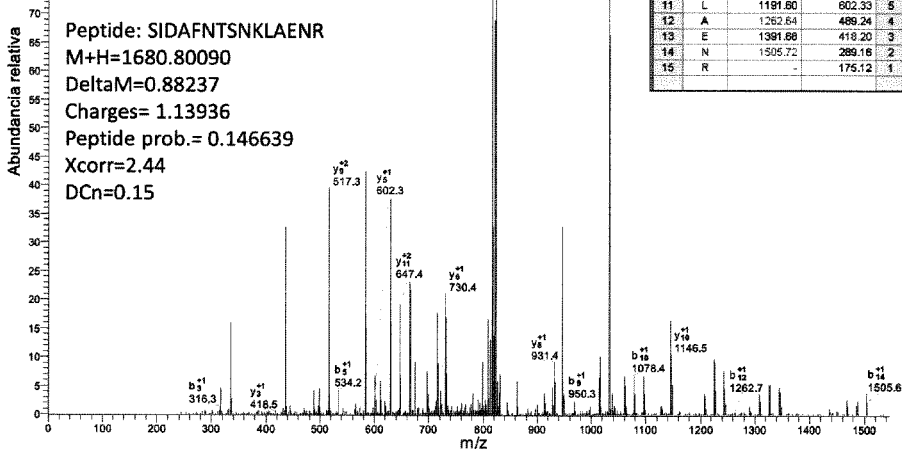
FIG. 8B

EXOSOMES DERIVED FROM RETICULOCYTES INFECTED WITH *PLASMODIUM* SP., METHOD FOR OBTAINING THEM AND USES THEREOF

RELATED APPLICATIONS

This application is a §371 national stage of PCT International Application No. PCT/EP2010/070800, filed Dec. 28, 2010, claiming priority of Spanish Patent Application No. ES P200931275, Dec. 28, 2009, the contents of each of which are hereby incorporated by reference into this application.

REFERENCE TO SEQUENCE LISTING

This application incorporates-by-reference nucleotide and/or amino acid sequences which are present in the file named "120627_5933_84296_Substitute_Sequence_Listing_SC.txt," which is 3 kilobytes in size, and which was created Jun. 27, 2012 in the IBM-PC machine format, having an operating system compatibility with MS-Windows, which is contained in the text file filed Jun. 27, 2012 as part of this application.

FIELD OF THE INVENTION

The present invention belongs to the field of vaccines for the prevention and prophylaxis against malaria, more specifically it relates to exosomes isolated from reticulocytes infected with *Plasmodium* sp., to methods for obtaining them and to the use thereof for the prevention and prophylaxis against malaria as well as to its use for the discovery and identification of novel *Plasmodium* antigens. The invention also refers to artificial exosomes comprising *Plasmodium* sp. antigens. Finally, the invention refers to specific antigens discovered by means of the exosomes obtained from reticulocytes infected with *Plasmodium* sp.

BACKGROUND OF THE INVENTION

*Plasmodium* sp. is the etiologic agent causing malaria, also known as "paludism". There are different species within the *Plasmodium* genus, some of which are innocuous. Other species, on the contrary, are highly infectious and are the cause of most of the human malaria cases worldwide. Among the latter, the most important species are *P. falciparum*, and *P. vivax*.

All the human *Plasmodium* species (*P. falciparum, P. vivax, P. malariae, P. ovale, P. knowlesi*) infect, to a greater or lesser extent, erythrocytes and/or the precursors thereof, reticulocytes, which require a process of maturation and differentiation to reach their final functional state as erythrocytes. Among the different *Plasmodium* species, there are some which have a higher reticulocyte infection capacity than others, such as *Plasmodium vivax* for example, which predominantly infects cells of this type.

During the process of maturation and differentiation of reticulocytes into erythrocytes, some proteins, which are not necessary for the latter, are sequestered in internal vesicles located in multi-vesicular bodies (MVBs) and are subsequently released into the extracellular medium as small nano-vesicles known as exosomes.

Recently, research on exosomes has been stimulated after the discovery that other cells, such as antigen-presenting cells, are capable of secreting nano-vesicles of this type, suggesting a role beyond the one originally described in the maturation and differentiation of reticulocytes. In fact, several studies with different types of cells have revealed that exosomes play a role in the regulation of the immune system since they transfer information between cells during immune response, and therefore, represent a new way of intercellular communication (1). In this line, the protective capacity of exosomes in experimental infections with *Toxoplasma gondii*, a member of the Apicomplexa phylum to which *Plasmodium* also belongs has been demonstrated (2).

Furthermore, several strategies based on the use of exosomes as prophylactic or immunostimulating agents for humans have been described (3).

Among others, WO9705900 discloses exosomes obtained from antigen-presenting cells such as B cells, macrophages or dendritic cells. The exosomes described in this document have the particularity that, since they are obtained from antigen-presenting cells, the antigens are presented in the MHC-I and MHC-II context.

Document EP1523990 in turn describes exosomes obtained from cancer cells (identified as texosomes) or from dendritic cells loaded or unloaded with antigens (this document refers to them as dexosomes).

WO2004014954 uses a different strategy since, in order to obtain exosomes showing a desired antigen in its surface, cells from the line CT26 (murine colon cancer) and cells from the line TA3HA (mouse mammary carcinoma) are transfected with recombinant viruses comprising in their genome the sequence which encodes the desired antigen (muc-1), which is thus expressed in the surface of the exosomes isolated from cells of this type.

WO0028001 describes exosomes obtained from mastocytes essentially lacking endogenous MHC molecules. The exosomes described in this document do express, however, recombinant MHCs in their surface.

Finally, WO2008092153 describes exosomes obtained from cancer cells which lack one or more immunosuppressive polypeptides normally present in exosomes.

The authors of the present invention have now developed a new strategy in the prevention and prophylaxis of malaria based on the use of exosomes isolated from reticulocytes of murine models or subjects infected with *Plasmodium*. These exosomes are obtained from peripheral blood infected with *Plasmodium* sp. or from in vitro cultures of reticulocytes previously obtained from said peripheral blood.

BRIEF DESCRIPTION OF THE DRAWINGS

FIG. 1: it depicts the characterization of exosomes isolated from mouse plasma. (A) Size analysis by dynamic light scattering. (B) Negative staining after fixing with 2% paraformaldehyde. The scale represents 100 nm.

DETAILED DESCRIPTION OF THE INVENTION

Figure 2:
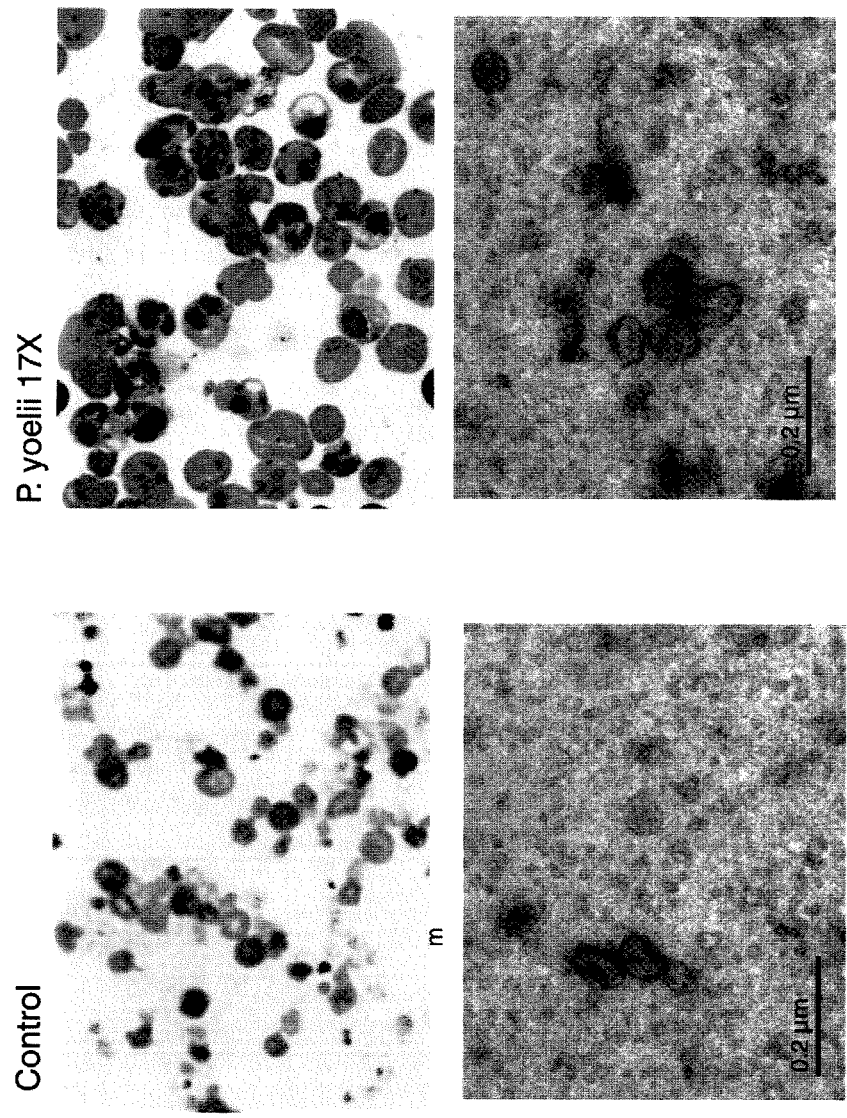
FIG. 2: (A) Giemsa staining of reticulocytes isolated from blood of control mice and mice infected with *P. yoelii* 17X. (B) EM image of negatively stained exosomes from reticulocytes. Scale bar represent 200 nm.

The first object of the present invention is represented by an exosome isolated from plasma reticulocyte culture which comprises at least one *Plasmodium* sp. antigen in its interior or in its surface (hereafter known as exosomes of the invention).

The exosomes of the invention have shown immunogenic capacity against malaria, so they have a high potential usefulness in the preparation of a vaccine for the prevention and prophylaxis of this disease.

The antigen or antigens present in the exosomes of the present invention can come from any *Plasmodium* species. In a particular embodiment of the invention, the antigen or antigens present in the exosomes come from *P. vivax, P. falciparum, P. malariae, P. ovale, P. yoelli, P. achiotense, P. achromaticum, P. aegyptensis, P. aeuminatum, P. agamae, P. anasum, P. atheruri, P. azurophilum, P. balli, P. bambusicolai, P. basilisci, P. berghei, P. bigueti P. brasilianum, P. brygooi, P. booliati, P. bubalis, P. bucki, P. coatneyi, P. cathemerium, P. cephalophi, P. chabaudi, P. chiricahuae, P. circularis, P. cnemidophori, P. coatneyi, P. coggeshalli, P. colombiense, P. corradettii, P. coturnix, P. coulangesi, P. cuculus, P. pogo, P. cyclopsi, P. cynomolgi, P. diminutivum, P. diploglossi, P. dissanaikei, P. dominicana, P. durae, P. egerniae, P. elongatum, P. eylesi, P. fabesia, P. fairchildi, P. fallax, P. fieldi, P. foleyi, P. forresteri, P. floridense, P. fragile, P. garnhami, P. gallinaceum, P. giganteum, P. giovannolai, P. girardi, P. gonatodi, P. gonderi, P. georgesi, P. gracilis, P. griffithsi, P. guanggong, P. gundersi, P. guyannense, P. heischi, P. hegneri, P. hermani, P. heteronucleare, P. hexamerium, P. holaspi, P. huffi, P. hylobati, P. icipeensis, P. inopinatum, P. inui, P. jefferi, P. josephinae, P. juxtanucleare, P. kempi, P. knowlesi, P. kentropyxi, P. leanucteus, P. lemuris, P. lophurae, P. lepidoptiformis, P. lygosomae, P. mabuiae, P. mackerrasae, P. maculilabre, P. major, P. marginaturn, P. matutinum, P. mexicanum, P. minasense, P. morulum, P. nucleophilium, P. octamerium, P. odocoilei, P. papernai, P. paranucleophilum, P. parvulum, P. pedioecetii, P. pelaezi, P. percygamhami, P. petersi, P. pifanoi, P. pinotti, P. pinorrii, P. pitheci, P. pitmani, P. polare, P. praecox, P. reichenowi, P. relictum, P. rhadinurum, P. rhodaini, P. robinsoni, P. rouxi, P. sandoshami, P. sasai, P. schweitzi, P. silvaticum, P. simium, P. semiovale, P. shortii, P. smirnovi, P. subpraecox, P. tenue, P. tejerai, P. tomodoni, P. torrealbai, P. traguli, P. tribolonoti, P. tropiduri, P. uilenbergi, P. watteni, P. wenyoni, P. vacuolatum, P, vastator, P. vaughani, P. vinckei, P. volans* or *P. youngi*.

In a preferred embodiment of the invention, the exosomes comprise antigens coming from *Plasmodium* species which infect humans, monkeys and/or rodents, i.e., in a preferred embodiment of the invention, said antigen or antigens present in the interior or in the surface of the exosomes belong to *Plasmodium vivax, Plasmodium falciparum, Plasmodium malariae, Plasmodium ovale, Plasmodium yoelli, P. berghei, P. brasilianum, P. chabaudi, P. cynomolgi, P. fragile, P. knowlesi* or *P. reichenowi*.

The exosomes of the present invention can be isolated from reticulocytes of any mammal infected with *Plasmodium* sp. although they are preferably isolated from human, monkey and/or mouse reticulocytes. A preferred embodiment contemplates the use of human reticulocytes to prevent, as far as possible, undesirable reactions when they are administered to human patients.

Another object of the present invention is represented by a method for obtaining the exosomes of the invention which comprises:
a) obtaining a blood sample infected with *Plasmodium* sp.,
b) optionally, isolating and culturing reticulocytes from the blood sample of a)
c) obtaining the fraction of exosomes derived from reticulocytes by means of sequential ultracentrifugation of the blood sample from a) or b).

In a particular embodiment the blood sample can be blood infected with *P. vivax, P. falciparum, P. malariae, P. ovale, P.*

*yoelli, P. achiotense, P. achromaticum, P. aegyptensis, P. aeuminatum, P. agamae, P. anasum, P. atheruri, P. azurophilum, P. balli, P. bambusicolai, P. basilisci, P. berghei, P. bigueti P. brasilianum, P. brygooi, P. booliati, P. bubalis, P. bucki, P. coatneyi, P. cathemerium, P. cephalophi, P. chabaudi, P. chiricahuae, P. circularis, P. cnemidophori, P. coatneyi, P. coggeshalli, P. colombiense, P. corradettii, P. coturnix, P. coulangesi, P. cuculus, P. popo, P. cyclopsi, P. cynomolgi, P. diminutivum, P. diploglossi, P. issanaikei, P. dominicana, P. durae, P. egerniae, P. elongatum, P. eylesi, P. fabesia, P. fairchildi, P. fallax, P. fieldi, P. foleyi, P. forresteri, P. floridense, P. fragile, P. garnhami, P. gallinaceum, P. giganteum, P. giovannolai, P. girardi, P. gonatodi, P. gonderi, P. georgesi, P. gracilis, P. griffithsi, P. guanggong, P. gundersi, P. guyannense, P. heischi, P. hegneri, P. hermani, P. heteronucleare, P. hexamerium, P. holaspi, P. huffi, P. hylobati, P. icipeensis, P. inopinatum, P. inui, P. jefferi, P. josephinae, P. juxtanucleare, P. kempi, P. knowlesi, P. kentropyxi, P. leanucteus, P. lemuris, P. lophurae, P. lepidoptiformis, P. lygosomae, P. mabuiae, P. mackerrasae, P. maculilabre, P. maior, P. marginatum, P. matutinum, P. mexicanum, P. minasense, P. morulum, P. nucleophilium, P. octamerium, P. odocoilei, P. papernai, P. paranucleophilum, P. parvulum, P. pedioecetii, P. pelaezi, P. percygarnhami, P. petersi, P. pifanoi, P. pinotti, P. pinorrii, P. pitheci, P. pitmani, P. polare, P. praecox, P. reichenowi, P. relictum, P. rhadinurum, P. rhodaini, P. robinsoni, P. rouxi, P. sandoshami, P. sasai, P. schweitzi, P. silvaticum, P. simium, P. semiovale, P. shortii, P. smirnovi, P. subpraecox, P. tenue, P. tejerai, P. tomodoni, P. torrealbai, P. traguli, P. tribolonoti, P. tropiduri, P. uilenbergi, P. watteni, P. wenyoni, P. vacuolatum, P. vastator, P. vaughani, P. vinckei, P. volans* or *P. youngi.*

However, in a preferred embodiment of the invention, the blood sample is infected with *Plasmodium vivax, Plasmodium falciparum, Plasmodium malariae, Plasmodium ovate, Plasmodium yoelli, P. berghei, P. brasilianum, P. chabaudi, P. cynomolgi, P. fragile, P. knowlesi, P. reichenowi.*

Although step b) of the method is optional it is a preferred option of the invention to carry it out. By performing step b) the exosomic fraction is purer in exosomes derived from reticulocytes. If step b) is not performed, the exosomic fraction may contain small traces of exosomes from other cellular types different from reticulocytes such as, for instance, dendritic cells.

The isolation of reticulocytes from the whole blood sample may be carried out by:
 i) centrifuging at 700-1000×g for 15-25 minutes,
 ii) centrifuging in Percoll gradient at 200-300 g for 25-35 min.

Isolation of reticulocytes in step b) can also be performed by means of a magnetic beads system. For instance, magnetic beads can be conjugated to anti CD71 antibodies since CD71 is a main surface marker of reticulocytes.

After the isolation of reticulocytes, these are cultured in vitro under common conditions.

Step c) of the method comprises sequential ultracentrifugation steps either from the blood sample from step a) or from the reticulocytes cultured in vitro from step b).

In a particular and preferred embodiment the sequential ultracentifugation comprises:
 i) centrifuging between 400-700×g for 15-25 minutes,
 ii) centrifuging between 900-1000×g for 15-25 minutes,
 iii) centrifuging between 10,000-14,000×g for 20-40 minutes,
 iv) centrifuging between 90,000-110,000×g for 1-3 hours,
 Optionally, after this first sequential ultracentrifugation, the resulting pellet is suspended in a buffer solution, preferably PBS, and filtered through a filter which discriminates the fraction of exosomes by particle size (the filter should have a pore size of about 0.20 µm). After this operation, it is preferably centrifuged again at 90000-11 000×g for 1-3 hours.

The sequential centrifugation must preferably be carried out at a low temperature of between 0-7° C. to preserve the integrity the proteins and the protein structures of the purified exosomes.

If the exosome are directly obtained from the whole blood, that is if step b) of the method is not performed, normally an exosome fraction mostly formed by exosomes derived from reticulocytes is obtained. However, this fraction can contain a minimum fraction of exosomes derived from other blood cell types.

Although the fraction obtained is sufficiently enriched in exosomes derived from reticulocytes, optionally, if an even more enriched fraction is desired, the fraction of exosomes obtained can be subjected to a method of purification by immunoisolation. Immunoisolation implies the use of specific antibodies against specific molecules of reticulocytes present in exosomes. In a particular embodiment, immunoisolation may be performed by means of using specific antibodies against the transferrin receptor.

The immunoisolation of the exosomes derived from reticulocytes may be carried out by magnetic beads coated with antibodies against the transferrin receptor. The exosomes derived from reticulocytes, once attached to the magnetic beads through the anti-transferrin receptor antibodies, can be separated from the latter by means of an acid treatment.

The analysis of the exosomes of the invention allows the discovery and identification of the antigens of *Plasmodium* sp. present in their interior or surface as demonstrated in the examples. In this sense, it is also an object of the present invention the use of the exosomes isolated from reticulocytes infected with *Plasmodium* sp. for the discovery and identification of *Plasmodium* sp. antigens.

One of the antigens identified in the present invention is protein Yir from *Plasmodium yoelli* which is the ortologue of protein Vir from *Plasmodium vivax*. From this protein the inventors have developed two Vir derived peptides which have been demonstrated to be antigenic upon immunizations of guinea pigs and capable of eliciting specific IgG immune responses recognizing *P. vivax*-infected reticulocytes from patients.

Therefore, it is also an object of the invention the Vir derived peptide having SEQ ID NO 1 or at least 85% homology with SEQ ID NO 1 as well as the Vir derived peptide having SEQ ID NO 1 or at least 85% homology with SEQ ID NO 2. These peptides have been called Lp1 and Lp2 respectively.

Another aspect of the present invention is an artificial exosome comprising at least one *Plasmodium* sp antigen in its interior or in its surface.

The artificial exosomes have been developed by known methods (de la Peña et al. 2009) comprising the *Plasmodium* antigens identified, namely Lp1 and Lp2, however any other *Plasmodium* antigen may be incorporated in the artificial exosomes formulation. The use of artificial exosomes reduces the risk of an autoimmune response occurring in the immunized patient.

In a preferred embodiment of the invention, the artificial exosomes are mainly coupled to antigens from *Plasmodium* species which infect monkeys, mice or humans, such as for example, *Plasmodium vivax, Plasmodium falciparum, Plasmodium malariae, Plasmodium ovale, Plasmodium yoelli, P. berghei, P. brasilianum, P. chabaudi, P, cynomolgi, P. fragile,*

*P. knowlesi, P. reichenowi*. In a preferred embodiment, the artificial exosomes comprise *P. vivax, P. falciparum, P. malariae* or *P. ovate* antigens.

A preferred embodiment of the invention is represented by an artificial exosome comprising a *Plasmodium* sp. antigen comprising Vir derived peptide having SEQ ID NO 1 or at least 85% homology with SEQ ID NO 1 and/or Vir derived peptide having SEQ ID NO 2 or at least 85% homology with SEQ ID NO 1.

Another object of the present invention is a pharmaceutical composition comprising the exosomes of the invention or the artificial exosomes of the invention and/or the peptides of SEQ ID NO 1 and/ SEQ ID NO 2 or peptides having at least 85% homology with SEQ ID NO 1 or SEQ ID NO 2 and at least one pharmaceutically acceptable excipient.

The excipients can be selected from carriers, supporting materials, lubricants, fillers, solvents, diluents, colorants, taste conditioners such as sugars, antioxidants and/or binders. The selection of these auxiliary materials and/or excipients and of the amounts which must be used will depend on the form of application of the pharmaceutical composition.

The pharmaceutical composition according to the invention can be adapted to any dosage form, either by oral route or by parenteral route, for example, by pulmonary route, by nasal route, by rectal route and/or by intravenous route. Therefore, the formulation according to the invention can be adapted for topical or systemic application, specifically for dermal, subcutaneous, intramuscular, intraarticular, intraperitoneal, pulmonary, buccal, sublingual, nasal, percutaneous, vaginal, oral or parenteral application.

A final object of the present invention is a vaccine against malaria comprising exosomes of the invention or the artificial exosomes of the invention and/or the peptides of SEQ ID NO 1 and/ SEQ ID NO 2 or peptides having at least 85% homology with SEQ ID NO 1 or SEQ ID NO 2.

The followings examples serve to illustrate the invention but do not intend to limit the scope thereof.

EXAMPLES

Example 1

Purification of Exosomes 1.1. Direct Purification from Mice Blood

The exosomes were purified from plasma obtained from mouse blood collected in EDTA. Plasmas of Balb/c mice infected and uninfected with the strains *P. yoelii* 17X and 17XL at 10-40% parasitemia were used. For the isolation of the exosomes, the serums were sequentially centrifuged at 500×g for 30 min, 12000×g for 35 min and at 100000×g for 2 hours at 4° C. The final precipitate was resuspended in PBS (usually 5× the original volume of serum), filtered through a 0.22-μm filter and centrifuged at 100000×g for 2 hours at 4° C. The precipitates were resuspended in 1XPBS and the amount of proteins recovered was determined by means of a Bradford assay. Approximately 5 micrograms of exosomes are obtained from 1.5 ml of serum. The obtained material is used immediately or is frozen by means of quick cooling and is stored at −80° C.

The exosomes were analyzed by means of dynamic light scattering (DLS) and electron microscopy (EM) to confirm their purity and to view their morphology (FIG. 1). For the DLS measurements, 50 μl of a 0.1 μg/μl suspension in PBS at 25° C. were analyzed using a Zetasizer Nano S (Malvern Instruments). The EM analyses were conducted from fresh exosome preparations fixed in 2% paraformaldehyde overnight at 4° C. The exosomes were placed on formvar grids for 1 minute before being washed in distilled water. The grids were negatively stained for 1 minute with a 2% solution of uranyl acetate in distilled water. After being completely dried, the grids were observed under a JEOL 1010 transmission electron microscope. Both techniques revealed homogenous populations of nano-vesicles with a diameter compatible to the size previously described for exosomes.

1.2. Purification from Mice In Vitro Cultured Reticulocytes

Exosomes were purified from supernatant of a reticulocyte culture. Reticulocytes were obtained from mice blood collected in EDTA. Blood of Balb/c mice uninfected and infected with the *P. yoelii* 17X strain at 20-40% parasitemia was used. To isolate the reticulocytes, blood was centrifuged at 700-1000×g for 20 min. After two washes in phosphate-buffered saline (PBS), reticulocytes from blood were purified by layering them on top of a Percoll/NaCl density gradient. To do so, five milliliters of Percoll solution (density, 1.096 g/mL) was placed in 15 mL tubes. Two milliliters of Percoll (density, 1.058 g/mL) was layered over this. Two ml of blood diluted in PBS to a final hematocrit of 50% were layered on top of each tube. Tubes were centrifuged at 250×g for 30 minutes at 4° C. Reticulocytes were collected from the interface of the two Percoll layers and washed twice with PBS.

Purified reticulocytes (FIG. 2 A) were cultured for 24 h at 37° C. in DMEM, supplemented with 5 mM glutamine, 3% calf serum, 50 U/mL penicillin, and 50 μg/mL streptomycin at a density of 1-5×$10^7$ cells/mL. To avoid any possible contamination by exogenous exosomes in the culture medium, the fetal bovine serum was precentrifuged (100 000×g o.n.). Exosomes were isolated from the supernatant by centrifugation at 500×g for 20 min, at 900-1000×g for 20 min, at 12 000×g for 30 minutes and at 100 000×g for 2 h at 4° C. The final pellet was resuspended in a large volume of PBS (usually 5× the original volume), filtered through a 0.22-μm filter and centrifuged at 100 000×g for 2 h at 4° C. The pellets were resuspended in PBS, and the amount of proteins recovered was determined by Bradford assay.

Exosomes have been analyzed by electron microscopy (EM) in order to confirm their purity and visualize their morphology (FIG. 2B). EM analysis was performed with fresh exosomes fixed in 2% PFA overnight at 4° C. Exosomes were then deposited onto formvar grids for 20 min before being washed with PBS. The grids were then fixed in glutaraldehyde 1% for 5 min, washed in distilled water and negatively stained for 5 min with a solution of uranyl-oxalate (pH=7) and for 10 min at 4° C. with uranyl acetate (4%)-methyl cellulose (2%). After being dried thoroughly, the grids were observed with a JEOL 1010 transmission electron microscope. This technique revealed a homogeneous population of vesicles in the sample with a diameter compatible with the size previously reported for exosomes.

1.3. Purification of Exosomes from Human In Vitro Cultured Reticulocytes

Human reticulocytes from peripheral blood were obtained from unprocessed blood bags from the Blood and Tissue Bank of Barcelona (www.bancsang.net). To obtain the samples, centrifugation was performed on Percoll density gradient following the method already described in example 1.2. Previously the samples were depleted of leukocytes using Plasmodipur filters (Eurodiagnostica).

In parallel to this methodology human reticulocytes were also concentrated by magnetic beads conjugated with anti-CD71 (main surface marker of reticulocytes) using the purification system Midi-MACS (Miltenyi Biotec) and following the manufacturer's specifications. Human reticulocytes concentrated by both methods, were maintained in different culture media (DMEM, RPMI) for 24 h, and the human reticulocytes derived exosomes (hREX) were concentrated from the supernatants by ultracentrifugation following the methodology described in example 1.2.

1.4. Purification from Human Reticulocytes Infected with *Plasmodium vivax*

Reticulocytes infected with mature forms of *P. vivax* were collected using the magnetic columns system Midi-MACS (Miltenyi Biotec) following the methodology described by Ribaut et al. (4). Infected reticulocytes were washed with incomplete medium and maintained for 24 h in different media (DMEM, RPMI).

Human *P. vivax* infected reticulocytes derived exosomes (hiREX) were concentrated from the supernatant by ultracentrifugation following the methodology described in example 1.3.

Example 2

Figure 3:
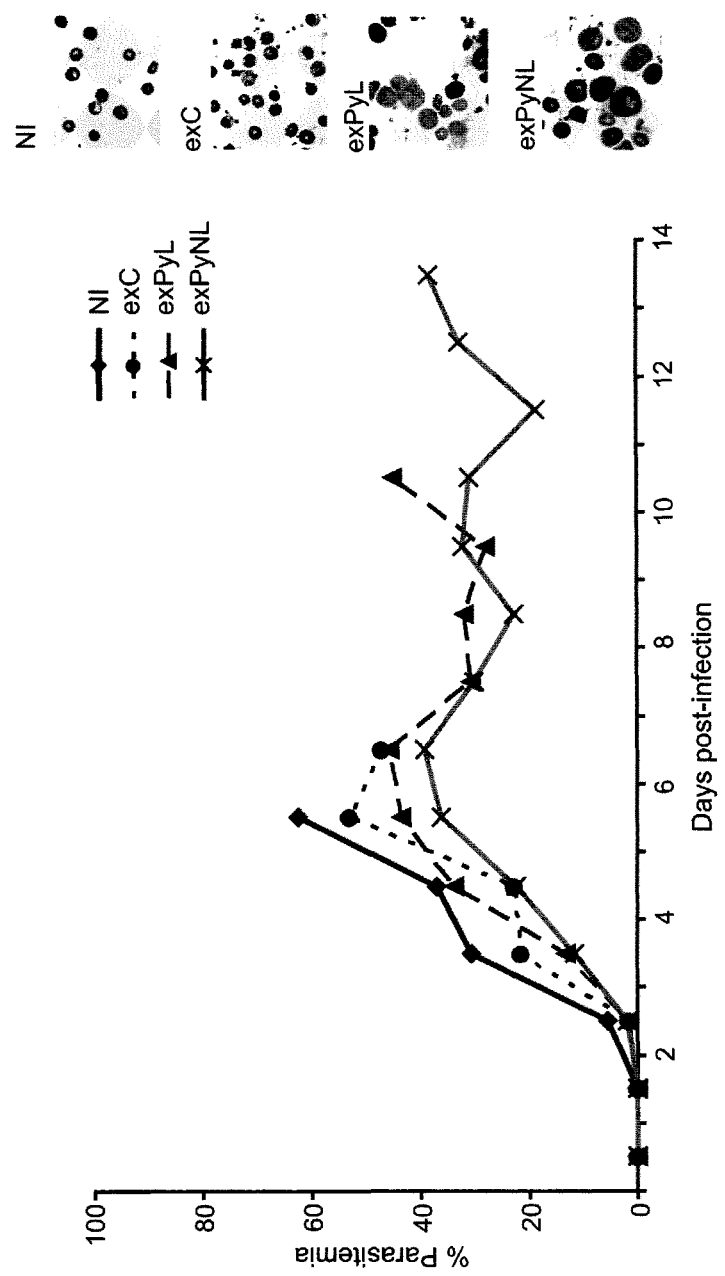
FIG. 3: it depicts the evolution over time of parasitemia and the analysis of cell tropism of mice immunized with exosomes. The parasitemia curves were calculated from the mean of 2 non-immunized control mice, 2 control mice immunized with exosomes isolated from blood of normal animals, 3 mice immunized with exosomes obtained from animals infected with the non-lethal strain of *P. yoelii*, and 3 mice immunized with exosomes obtained from animals infected with the lethal strain of *P. yoelii*. Giemsa staining for peripheral blood smears on the day prior to sacrificing in a representative animal of each group.

Immunogenic Properties of the Exosomes 2.1. Immunogenic Properties of Exosomes Obtained by Direct Purification from Mice Blood Balb/c mice were immunized with exosomes derived from the blood of uninfected mice (exC) and mice infected with exosomes of the non-lethal (exPyNL) and lethal (exPyL) strain as obtained in example 1.1. For the immunizations, the mice received 5 µg intravenous (i.v.) injections of exosomes in 100 µl of PBS after having been anesthetized with a combination of Ketamine (100 mg/Kg) and Midazolam (5 mg/Kg) injected intraperitoneally. Two experiments with exosomes have been performed with groups of 4-6 Balb/c mice (9-11 weeks of age) (i.v) immunized at 20-day intervals with two doses of exosomes. The non-immunized (NI) mice were not treated. Twenty days after the second immunization, all the mice were infected with $5 \times 10^5$-$10^6$ parasites of the lethal strain (*P. yoelii* 17XL) and the parasitemia was controlled daily. Outstandingly, half the mice immunized with exosomes of each strain showed differences in the parasitemia curves with a longer survival time when compared to the NI and exC mice (FIG. 3). Furthermore, the mice immunized with exosomes of infected animals showed not only an increase of reticulocytemia but also a change of cell tropism of the lethal strain of normocytes for reticulocytes (Table I).

TABLE I

Groups of Balb/c mice were immunized with exosomes from blood of uninfected animals (exC, n = 4) and mice infected with Py17XL (exPyL, n = 4) and Py17XNL (exPyNL, n = 6). The non-immunized (NI) mice were not treated. The percentage of infected reticulocytes and reticulocytemia were measured on the day prior to death. The results of the different groups are expressed with mean ± standard error.

|  | Days survived after the death of non-immunized animals | % of infected reticulocytes | Reticulocytemia |
| --- | --- | --- | --- |
| NI |  | 0.65 ± 0.92 | 0.6 ± 0.85 |
| exC | 0.5 ± 0.33 | 3.08 ± 1.72 | 3.02 ± 1.48 |
| exPyL | 2.5 ± 1.37 | 49.15 ± 21.46 | 30.98 ± 16.11 |
| exPyNL | 3.5 ± 1.29 | 35.57 ± 18.66 | 23.68 ± 12.83 |

Figure 4:
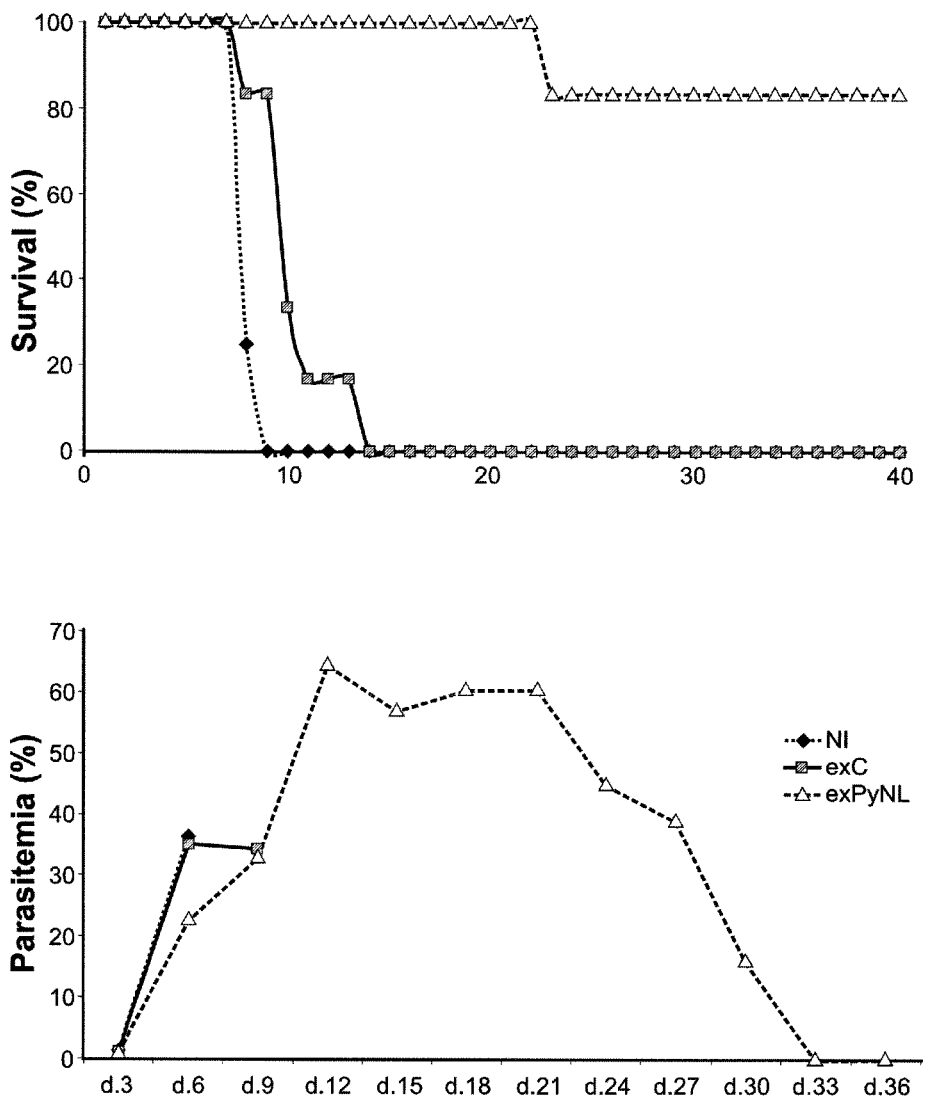
FIG. 4: A) Survival curve and (B) time-course parasitemia, of *Plamodium yoelii* 17XL infections of groups of BALB/C mice previously immunized with exC (n=6) and exPyNL (n=6). Non-immunized mice (n=5) were untreated.

2.2. Immunogenic Properties of Exosomes Obtained by Purification of In Vitro Cultured Reticulocytes Balb/c mice were immunized with exosomes obtained from a culture of reticulocytes non-infected (exC) and infected with the non-lethal *P. yoelii* 17X strain (exPyNL) as obtained in example 1.2. For the immunizations, mice were injected subcutaneously (s.c.) with 10 µg of exosomes and 10 µg of CpG ODN-1826. Twenty days after, mice were immunized with 5 µg of exosomes. Twenty days after the second immunization, all mice were infected with $5 \times 10^5$ *P. yoelii* 17XL and parasitemia was followed daily. Two experiments have been performed with groups of 6 female BALB/c mice (9-11 weeks of age) immunized. Non immunized mice (NI) were untreated. Remarkably, 5/6 mice immunized with exosomes from reticulocytes infected with *P. yoelii* 17X survived to an infection with the lethal parasite *P. yoelii* 17XL (FIG. 4).

Example 3

Humoral and Cellular Response 3.1—Humoral IgG Immune Response and Cellular Immune Response Elicited by Exosomes Directly Purified from Mice Blood After demonstrating the immunogenic capacity of the exosomes purified in example 1.1, experiments were initiated to evaluate if the protective responses were associated with humoral and/or cellular immune response.

Figure 5:
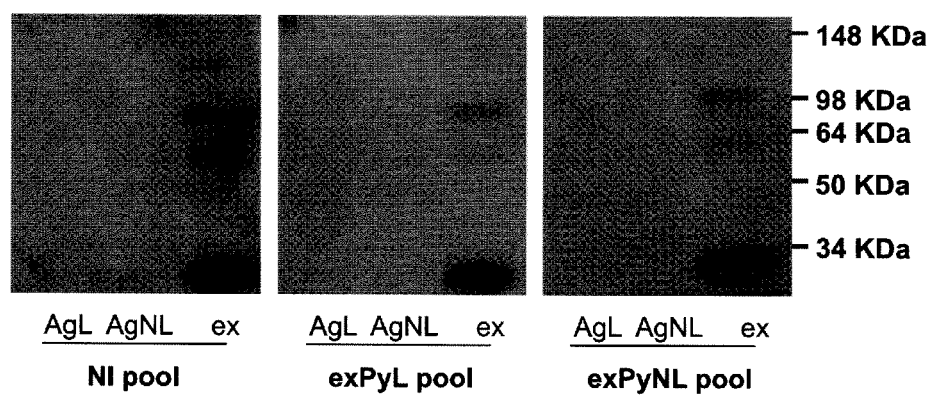
FIG. 5: Western blot analysis of the response of anti-*P. yoelii* IgG antibodies in the serum of animals immunized with exosomes. The samples were collected by maxillary puncture on day 20 after the second immunization. Each panel corresponds to a mixture of serums of each group of animals used in these experiments. In the Western blot, total antigen obtained from the non-lethal (AgNL) and lethal (AgL) strains of *P. yoelii* was used and the responses of IgG antibodies were detected by means of using goat serum conjugated to alkaline phosphatase and produced against mouse IgG.

To study the production of specific antibodies, sera were collected on day 20 prior to the second immunization and were stored at −20° C. Serum mixtures of the NI, exC, exPyNL and exPyL groups of animals were used to analyze the circulating anti-*P. yoelii* antibodies induced by the immunization with exosomes. Western blots were performed using a total *P. yoelii* antigen lysate obtained by lysing infected erythrocytes with 1.5 M $NH_4CL$, 0.1 M $KHCO_3$ and 0.01 M EDTA followed by several freezing and thawing cycles. Mice immunized with exosomes coming from non-lethal infection produced specific IgG antibodies against *P. yoelii* antigens of both strains (FIG. 5). As expected, no antibodies against *P. yoelii* were detected in the serums of non-immunized animals.

Figure 6:
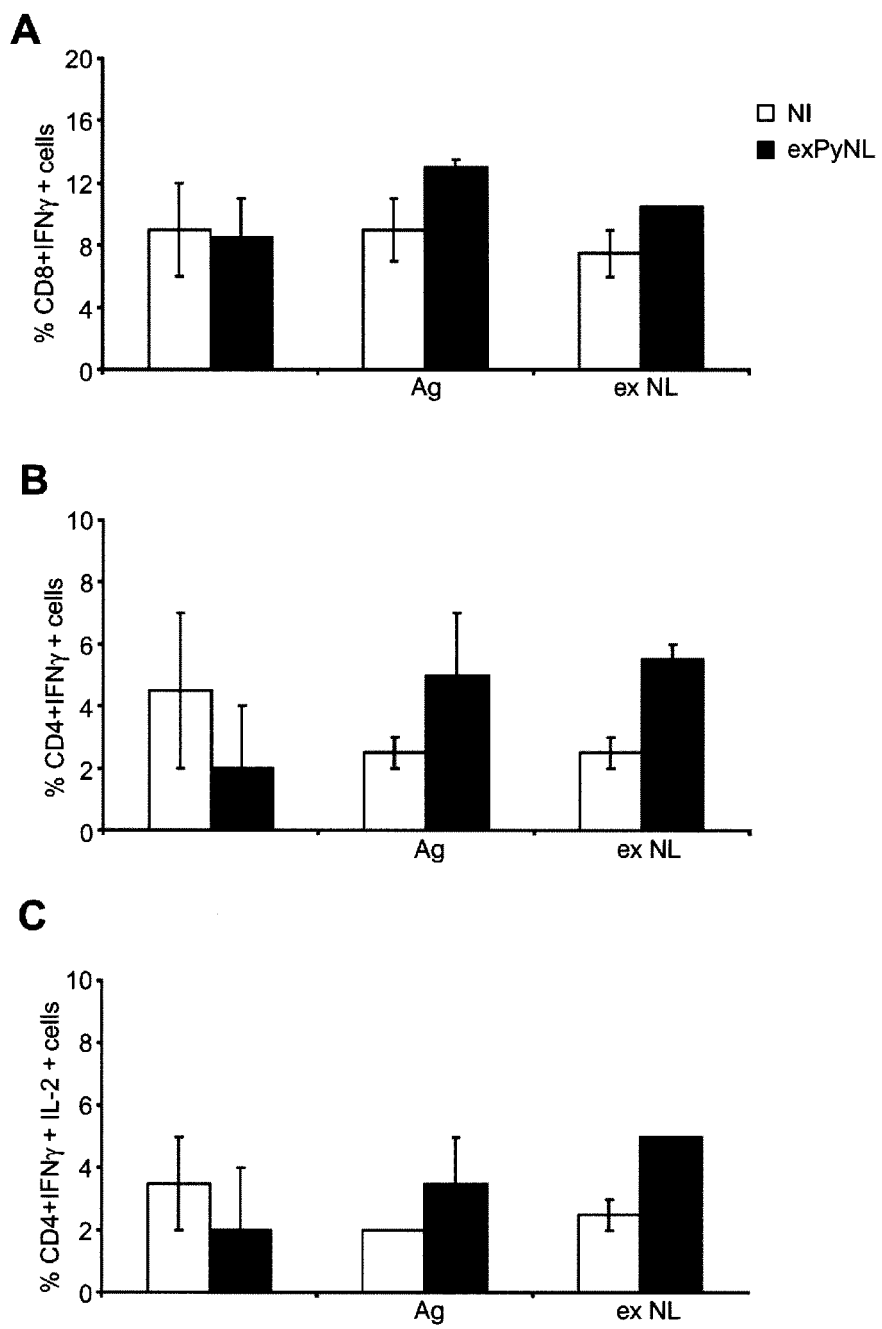
FIG. 6: it depicts an intra-cellular staining analysis of T, CD4+ and CD8+ cells in animals immunized with exosomes from blood of mice infected with the non lethal strain of *P. yoelii*. Balb/c mice were immunized with 5 micrograms of PyNL exosomes in CpG-ODN. Two weeks after the first immunization, a boost with 5 micrograms of exosomes without CpG-ODN was performed. (A) The percentage of $CD8^+$ IFN-$\gamma^+$ was calculated after an in vitro re-stimulation, intracellular staining and flow cytometry analysis. The percentage of $CSFE^{lo}$ lymphocytes that are $CD4^+$ IFN-$\gamma^+$ is represented in (B) and that of $CD4^+$ IFN-$\gamma^+$ IL-2 in (C). The data correspond to one experiment and is expressed as the mean±standard error of 3 non-immunized mice and 3 mice immunized with exosomes coming from mice infected with the non-lethal exPyNL strain.

The production of cytokines of individual cells to evaluate the cellular immune response was performed by means of intracellular staining. Twenty days after the second immunization, spleen cells (splenocytes) of immunized animals were seeded in triplicate on 96-well plates ($5 \times 10^5$ cells/well). The splenocytes were cultured in DMEM medium supplemented with 10% fetal calf serum (FCS) inactivated by temperature, HEPES (10 mM), L-glutamine (2 mM), sodium pyruvate (1 mM), 23-mercaptoethanol (50 µM), and penicillin-streptomycin (0.1 mM), and in the presence or absence of 10 µg/ml of *P. yoelii* antigen or 5 µg of a frozen exosome preparation. To analyze the proliferation, the cells were stained with 5-6-carboxyfluorescein diacetate succinimidyl ester (CFSE) using the vybrant CFDASE cell tracer kit (Invitrogen) prior to the culture. The plates were incubated for 72 hours at 37° C. and with phorbol myristate acetate (50 ng/ml), ionomycin (500 ng/ml) and brefeldin A (10 µg/ml) in the last 4 hours. The cells were collected, washed and stained for 20 minutes to detect different surface markers using antibodies conjugated to different fluorophores. After two washes with PBS/BSA, the cells were fixed for 20 min at room temperature with cytofix/cytoperm (BD Biosciences) and were then washed and resuspended in a perm/wash solution which permeabilizes them. After the permeabilization, the cells were stained for 30 minutes with specific conjugated antibodies for different cytokines. The samples were analyzed in a FACS Calibur. The visual examination of the color and amount of cells in the wells after 72 hours of culture revealed a higher proliferative response in exPyNL splenocytes only in the presence of exosomes and of *P. yoelii* antigen. The number of $CD8^+$ T splenocytes which produced IFN-γ increased in animals immunized with exPyNL, and after restimulation, with exosomes and total P. yoelii antigen (FIG. 6A). CD4+ proliferative T Cells (CSFE low) which produce IFN-γ, alone or in combination with IL-2, are detected in a higher number in the same group of animals after the restimulation with total P. yoelii antigen and exosomes (FIG. 6B, 6C).

3.2. Humoral IgG Immune Response Elicited by Exosomes Purified from In Vitro Cultured Reticulocytes This example shows that exosomes purified in example 1.2 are capable of eliciting parasite-specific humoral IgG immune responses recognizing mature stages of P. yoelii-infected red blood cells (pRBCs).

Figure 7:
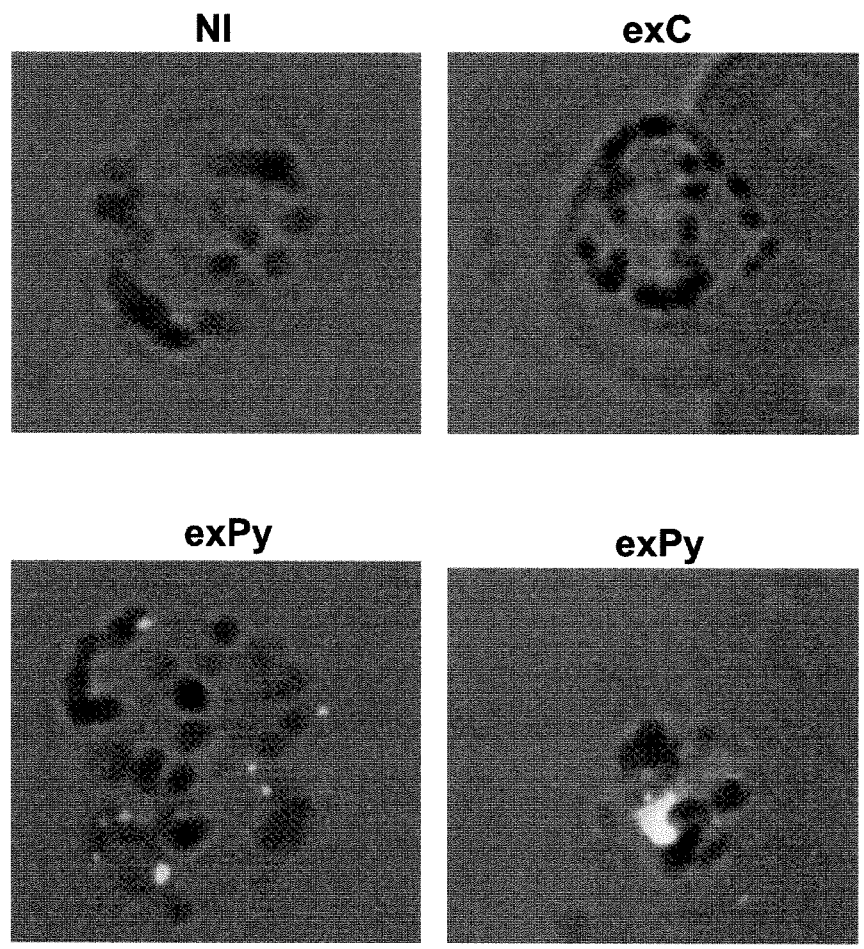
FIG. 7: Bright-field and fluorescence images of immune sera recognizing a 17XL-pRBC. NI=serum from a non-immunized mouse; exC=serum from a mouse immunized with exosomes from a non-infected mouse REX; exPy I=serum from two mice immunized with REX from a *P. yoelii* NL-infected animal.

Humoral IgG immune response elicited by exosomes was studied by immunofluorescence using sera from immunized mice collected 20 days after immunization and tested for parasite recognition. Immunofluorescence assays were performed on 17XL infected blood smears fixed with cold methanol and air-dried before blocking with 5% BSA/PBS for 30 min at RT. Slides were incubated with mouse sera diluted 1/10 in 0.5% BSA/PBS o.n. at 4° C. and for 1 h at RT. Reacting IgG were detected using an anti-Mouse IgG antibody conjugated to Alexa Fluor 488 (Invitrogen) diluted 1/200 for 1 h at RT. After washing, nuclei were stained with DAPI (Invitrogen, 5 mg/mL) at RT for 7 min. Sera recognizing pRBCs were imaged for bright-field and green fluorescence using a Leica TCS-SL microscope fitted with an inverted 63× oil objective. Sera from non-immunized mice and from mice immunized with exosomes from uninfected animals were used as negative controls. As shown in FIG. 7, immunizations with exPy elicited IgG antibodies capable of recognizing infected red blood cells.

Example 4

Proteomic Analysis of the Antigens

In addition to generating data on the immunogenicity of exosomes in experimental infections of malaria using the murine model of Balb/c—P. yoelii, data which demonstrate that the exosomes obtained from mice infected with P. yoelii or exosomes obtained from a patient with P. vivax contains antigens of the parasite have also been generated. To that end, 5 microgram aliquots of purified exosomes of uninfected mice, mice infected with the lethal and non-lethal strain of P. yoelii, a healthy human volunteer and a patient with P. vivax malaria, were analyzed by mass spectrometry.

4.1. Analysis by Mass Spectrometry Coupled to Liquid Chromatography.

Figure 8C:
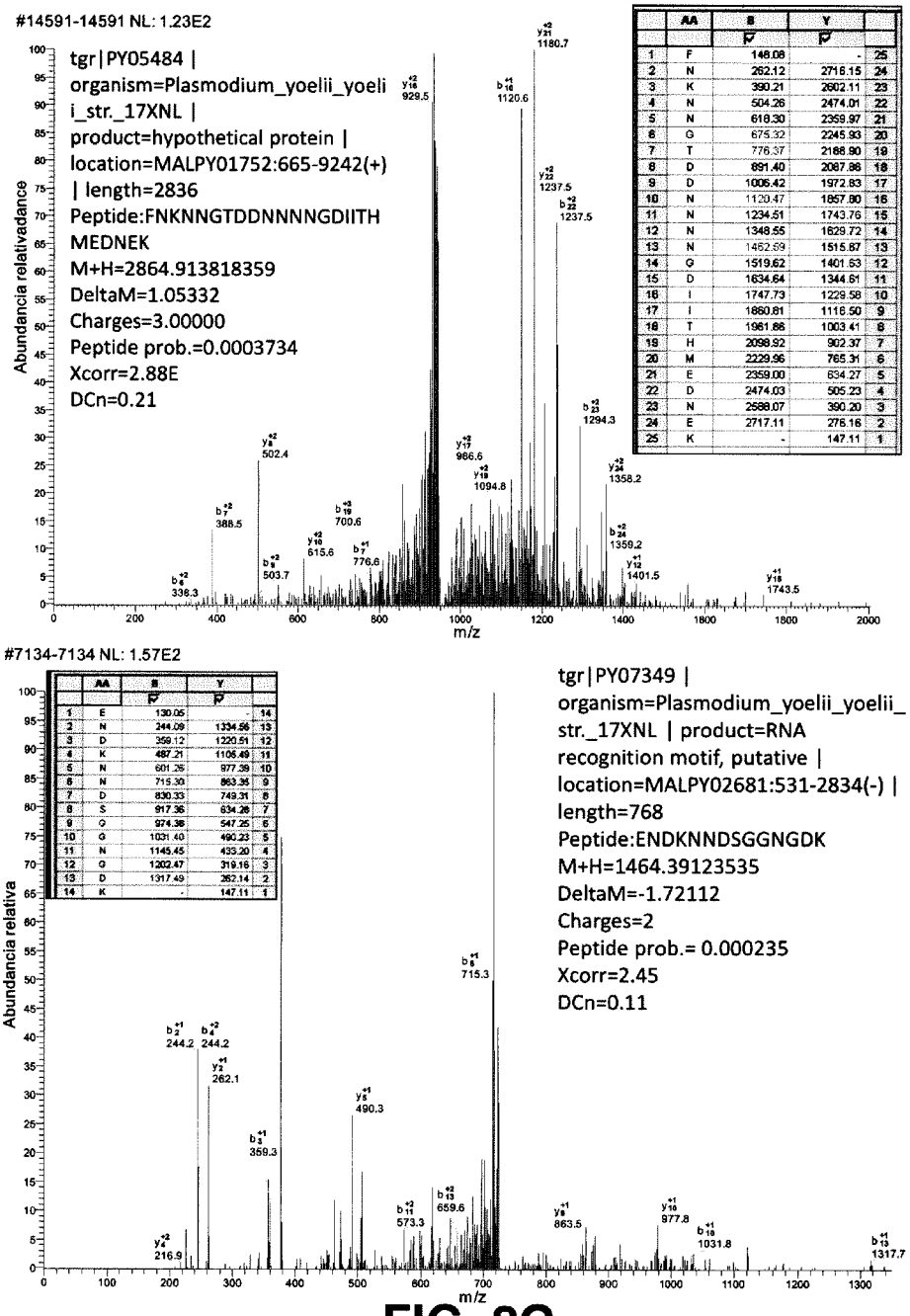
FIG. 8: (A)-(D) MS/MS spectrum resulting from the proteomic analysis of the antigens present in exosomes derived from peripheral blood coming from mice infected with *P. yoelii* and from a patient infected with *P. vivax*. The bioinformatic analysis of the spectrum confirms the presence of both *P. yoelii* and *P. vivax* antigens in the exosome samples analyzed.
Figure 8D:
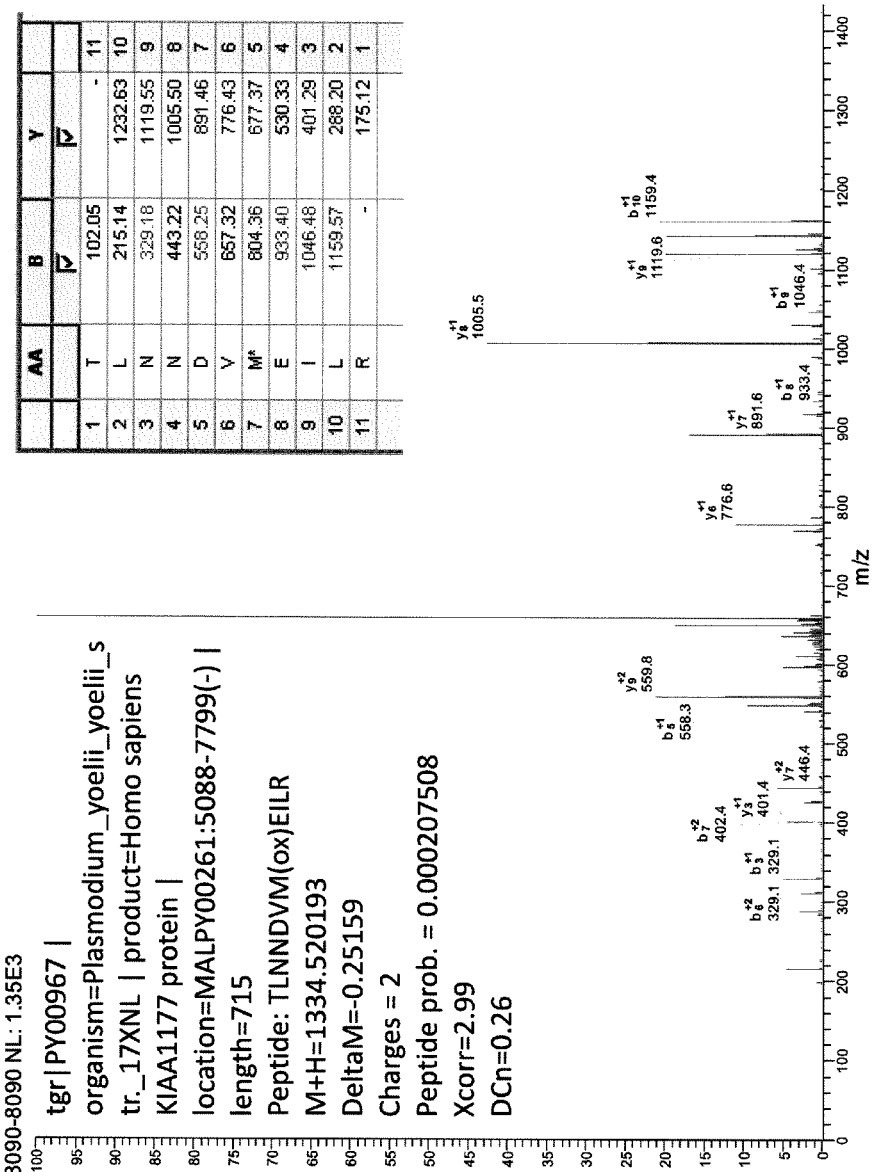

The exosome preparations were resuspended in 0.4 M $NH_4HCO_3$ in 8M urea. The samples were reduced with 5 mM DTT for 15 minutes at 50° C., alkylated with 10 mM iodoacetamide for 30 minutes at room temperature and diluted with HPLC grade water until obtaining a urea concentration of 1 M. After digesting for 16 hours with trypsin having a sequencing purity of 1/50 (enzyme/protein ratio), the reaction was ended by adding 1% formic acid (FA) (5). The samples were desalinated with POROS R2 ziptips (6) and were dried in an vacuum pump. The samples were subsequently resuspended in 0.1% FA (secured to a 2D LC-MS system (LC—Eksigent 1D-plus, MS—Thermo Fisher LTC) XL with ETD, ESI source—Triversa, Adivion). The samples were individually placed in a strong cation exchange (SCX) column (5 µL, Optimized Technologies), and automatically eluted by means of injecting increasing concentrations of NaCl (0-500 mM NaCl in 5% acetonitrile/0.5% FA). The eluted peptides were trapped and washed in a homemade C18 column (1 cm, 75 µm, Phenomenex Luna C18, 5 µm). The separation was achieved by means of a C18 capillary column (20 cm, 75 µm, Phenomenex Luna C18, 5 µm) in a linear gradient of ACN with 0.1% FA. The spectra were collected in the data-dependent acquisition mode (FIG. 8).

4.2. Bioinformatic Analysis

The MS/MS spectra (FIG. 5) were converted to DTA format and send to a database search using Sequest (Available in Bioworks 3.3.1, Thermo Fisher Scientific). The databases used for P. vivax and P. yoelii were those most recently released in PLasmoDB (http://plasmodb.org), and those of contaminating sequences such as human keratin, porcine trypsin, culture medium proteins were searched in (http://www.ebi.ac.uk/IPI/IPIhelp.html or http://www.ncbi.nlm.nih.gov/sites/entrez?db=Protein&itool=toolbar). All the sequences were concatenated to the reverse version to allow calculating false positives (7). The data obtained were filtered to obtain a false positives error level of approximately 1-2%.

Outstandingly, exosomes obtained from infected mice or from the patient with P. vivax revealed the presence of *Plasmodium* proteins (Table II). The data of the individual spectra validated by 100% that these peptides correspond to *Plasmodium* proteins.

All these results unequivocally demonstrate that the exosomes contain proteins of the parasite which causes malaria, including human malaria caused by P. vivax, and that they are capable of presenting antigen, generating immune and protective responses in a murine model.

TABLE II

| Accession number/description | Total number of peptide | Total number of spectra | xcorr sum | Peptide probability |
|---|---|---|---|---|
| tgr__PY00291 product__SERA__3__location__MALPY00082__1581__5430__+___length__1205 | 22 | 47 | 87.127 | 6.75E−11 |
| tgr__PY05787 product__putative cell division cycle ATPase__location__MALPY01892__3938__7174____length__1079 | 1 | 1 | 3.969 | 2.66E−09 |
| tgr__PY00292 product__Papain family cysteine protease__putative__location__MALPY00082__7268__10921__+___length__1133 | 18 | 36 | 70.545 | 3.75E−09 |
| tgr__PY02883 product__merozoite surface protein__9 precursor__putative__location__MALPY00811__3609__5645____length__679 | 10 | 20 | 37.951 | 9.73E−05 |
| tgr__PY05999 product__octapeptide__repeat antigen__location__MALPY01986__761__2980____length__740 | 9 | 15 | 31.953 | 5.02E−05 |
| tgr__PY03885 product__lactate dehydrogenase__location__MALPY01158__507__1457____length__317 | 9 | 25 | 38.922 | 2.21E−10 |

TABLE II-continued

| | Peptide (Hits) | | Score | P (pro) |
|---|---|---|---|---|
| tgr_PY05748 product_merozoite surface protein 1 precursor_location_MALPY01871_991_6309_____length_1773 | 9 | 14 | 33.698 | 7.54E-07 |
| tgr_PY00427 product_3_nucleotidase/nuclease_location_MALPY00119_10126_11112_____length_329 | 7 | 14 | 27.502 | 8.52E-05 |
| tgr_PY00293 product_Papain family cysteine protease_putative_location_MALPY00082_12343_16499__+___length_1224 | 7 | 10 | 25.306 | 0.000569 |
| tgr_PY04614 product_heat shock protein 60_location_MALPY01423_3332_5272__+___length_580 | 6 | 8 | 20.313 | 4.49E-06 |
| tgr_PY02351product_Y13180 multicatalytic endopeptidase_location_MALPY00643_11313_12796_____length_279 | 5 | 10 | 19.382 | 3.76E-07 |
| tgr_PY01759 product_hypothetical protein_location_MALPY00474_2572_10368_____length_2599 | 3 | 4 | 8.462 | 1.93E-05 |
| tgr_PY06307product_hypothetical protein_location_MALPY02121_3570_5407_____length_415 | 3 | 6 | 11.238 | 1.98E-11 |
| tgr_PY03639 product_cell division cycle protein 48 homolog_location_MALPY01071_977_3580__+___length_816 | 3 | 4 | 11.588 | 0.000967 |
| tgr_PY04190 product_proteasome subunit alpha Type 6_B_location_MALPY01255_298_1500__+___length_261 | 3 | 5 | 8.93 | 4.95E-05 |
| tgr_PY03212 product_proteasome beta_subunit_putative_location_MALPY00917_16257_17084__+___length_276 | 3 | 3 | 11.273 | 1.32E-05 |
| tgr_PY00275 product_hypothetical protein_location_MALPY00076_8839_9981_____length_381 | 2 | 3 | 7.002 | 0.000364 |
| tgr_PY06203 product_blood_stage membrane protein Ag_1_location_MALPY02079_1480_3304_____length_550 | 2 | 3 | 6.878 | 0.000256 |
| tgr_PY03709 product_Fructose_bisphosphate aldolase class_I_location_MALPY01091_9881_11154__+___length_410 | 2 | 3 | 5.899 | 0.000107 |
| tgr_PY03625 product_secreted blood_stage antigen pAg_3_location_MALPY01062_3866_5117__+___length_355 | 2 | 5 | 7.153 | 0.000172 |
| tgr_PY06158 product_heat shock protein 70_location_MALPY02061_6044_8092_____length_683 | 2 | 5 | 7.282 | 3.55E-06 |
| tgr_PY01014 product_retinitis pigmentosa GTPase regulator_like protein_location_MALPY00271_17200_19412_____length_675 | 2 | 4 | 9.099 | 2.83E-06 |
| tgr_PY06644 product_enolase_location_MALPY02281_2234_3769__+___length_456 | 2 | 2 | 7.82 | 0.000551 |
| tgr_PY00267 product_proteasome subunit alpha type 1_location_MALPY00076_6844_7789__+___length_246 | 2 | 4 | 6.468 | 2.06E-05 |
| tgr_PY03280 product_glyceraldehyde_3_phosphate dehydrogenase_location_MALPY00935_13110_14374__+___length_338 | 2 | 2 | 6.064 | 1.14E-06 |
| tgr_PY00768 product_26S proteasome subunit 4_like protein_location_MALPY00207_17148_18892_____length_448 | 1 | 2 | 4.212 | 3.48E-05 |
| tgr_PY00622 product_rhoptry associated protein 1_location_MALPY00169_2382_4208_____length_609 | 1 | 2 | 3.592 | 3.04E-05 |
| tgr_PY06837 product_putative T_complex protein beta subunit_location_MALPY02390_2164_4102__+___length_536 | 1 | 1 | 3.733 | 9.08E-05 |
| tgr_PY06834 product_putative yir4 protein_location_MALPY02388_4468_5607__+___length_315 | 1 | 1 | 3.588 | 0.00064 |
| tgr_PY06423 product_hypothetical protein_locaton_MALPY02180_138_4521_____length_1461 | 1 | 1 | 4.281 | 0.000742 |
| tgr_PY06767 product_proteosome PSMB5/8 protein_location_MALPY02351_3402_4355__+___length_288 | 1 | 2 | 4.167 | 1.31E-07 |
| tgr_PY04294 product_hypothetical protein_location_MALPY01297_4689_6543__+___length_365 | 1 | 2 | 3.763 | 0.000269 |
| tgr_PY05295 product_hypothetical protein_location_MALPY01675_6685_9672_____length_792 | 1 | 2 | 4.502 | 5.97E-05 |
| tgr_PY03834 product_AhpC/TSA family_putative_location_MALPY01137_2824_4703_____length_423 | 1 | 2 | 5.318 | 1.52E-12 |

| | Reference | Peptide (Hits) | Score | P (pro) |
|---|---|---|---|---|
| *Plasmodium vivax* | gb\|PVX_116515\|organism = Plasmodium_vivax_Sal-1\|product = hypothetical protein, conserved\|location = CM000453: 1038825-1043220(−)\|length = 1422 | 2 (2 0 0 0 0) | 2.02E+01 | 0.00014688 |
| | gb\|PVX_082575\|organism = Plasmodium_vivax_Sal-1\|product = isoleucyl-tRNA synthetase, putative\|location = CM000453: 827063-830683(+)\|length = 1206 | 2 (0 2 0 0 0) | 1.61E+01 | 0.00037904 |
| | REVgb\|PVX_122470\|organism = Plasmodium_vivax_Sal-1\|product = hypothetical protein, conserved\|location = CM000455: 598129-601995(+)\|length = 1152 | 3 (1 0 2 0 0) | 2.22E+01 | 1.59E-05 |
| | REVgb\|PVX_084425\|organism = Plasmodium_vivax_Sal-1\|product = hypothetical protein, conserved\|location = CM000454: 285733-288600(−)\|length = 955 | 2 (1 1 0 0 0) | 1.82E+01 | 7.96E-05 |
| | REVgb\|PVX_087755\|organism = Plasmodium_vivax_Sal-1\|product = hypothetical protein, conserved\|location = CM000442: 119705-124640(+)\|length = 1640 | 1 (1 0 0 0 0) | 1.02E+01 | 0.00057842 |

Example 5

Analysis of the Vir Protein the Ortologue of Yir Protein Identified in the Exosomes Derived from Reticulocites Infected with *Plasmodium yoelli*

One of the proteins identified in example 4 in *Plasmodium yoelli* was protein Yir. Yir are ortologues to Vir proteins from *Plasmodium vivax* (8). This example, provides data supporting that Vir proteins are immunogenic in natural infections, antigenic upon immunizations of mice and capable of eliciting specific IgG immune responses recognizing *P. vivax*-infected reticulocytes from patients. This data also support that exosomes derived from reticulocytes infected with *Plasmodium* sp. are indeed useful for the discovery of *Plasmodium* sp.

5.1. Vir Peptide Sequences and Bioplex Assay

Figure 9:
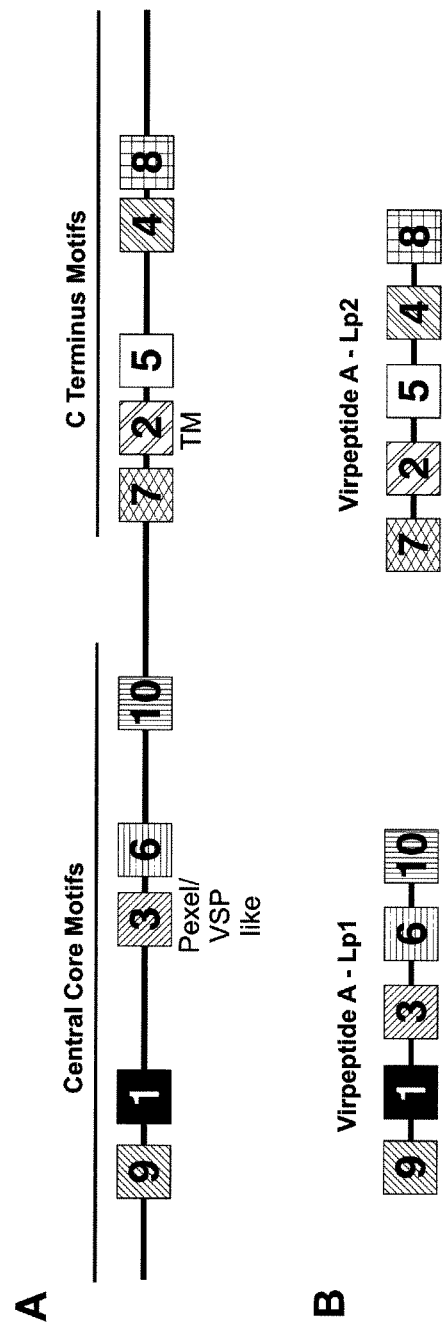
FIG. 9: A) Schematic representation of the Vir multigenic family conserved motifs. B) Schematic representation of the Virpeptide LP1(left) and Virpeptide LP2 (right).

According to MEME models previously used and reported by the inventors in the issue describing the complete genome sequence of *P. vivax* (9), Vir proteins have an archetypical conserved motif organization. Motifs 1 and 4 to 10 are predicted to be globular domains, motif 2 encodes hydrophobic amino acids typical of TM domains and motif 3 contains a Pexel-like sequence (FIG. 9A). Based on these conserved motifs two long peptides were designed, called Lp1 (SEQ ID NO 1) and Lp2 (SEQ ID NO 2). Lp1 contains the central core conserved motifs and Lp2 contains the C-terminus conserved motifs. These motifs are flanked by non immunogenic linker sequences and the conserved order of the motifs is maintained in the synthetic long peptides (FIG. 9B).

The sequence of Lp1 and Lp2 is represented as follows:

```
Lp1- (SEQ ID NO 1):
VKELCKKLVRNLKKISCIYLNYWLYDQIKERKDLHDYEKNYDTIKCCEKYCTYVTYIKSLYE

YDPKDLLSKLDC

Lp2-
                                                        (SEQ ID NO 2)
IADSPGTLGTVHEELDSNEFRNIIMVVGVMMTFFELYKFTPVGAFFRGGRGRVHRIPRSF

HGQFPGKRKGKIFEHNYYEEYEKELAMYGSEFLDSQMDRYYLNYQPDQDSYY
```

These peptides have been used in a Bioplex assay to check their immunogenity properties using sera from *P. vivax* patients from different endemic regions. BioPlex carboxylated beads (Bio-Rad) were covalently coated with the two long peptides following the manufacturer's instructions (BioPlex Amine Coupling Kit). Coupled beads were analysed as described by Fernandez-Becerra et al., 2010 (9). Briefly, aliquots of 50 µl, corresponding to 5,000 coated beads were used for each assay. Plasma samples were diluted 1:50 in assay buffer and 50 µl aliquots added to the beads (final plasma dilution 1:100). Aliquots of 50 µl of Biotinylated human IgG antibody (Sigma) diluted 1:7500 and of phycoerythrin conjugated streptavidin diluted to 2 µg/ml were used in subsequent incubations. Beads were re-suspended in 125 µl of assay buffer (BioRad) and analysed on the BioPlex100 system and results were expressed as median fluorescent intensity (MFI).

Figure 10:
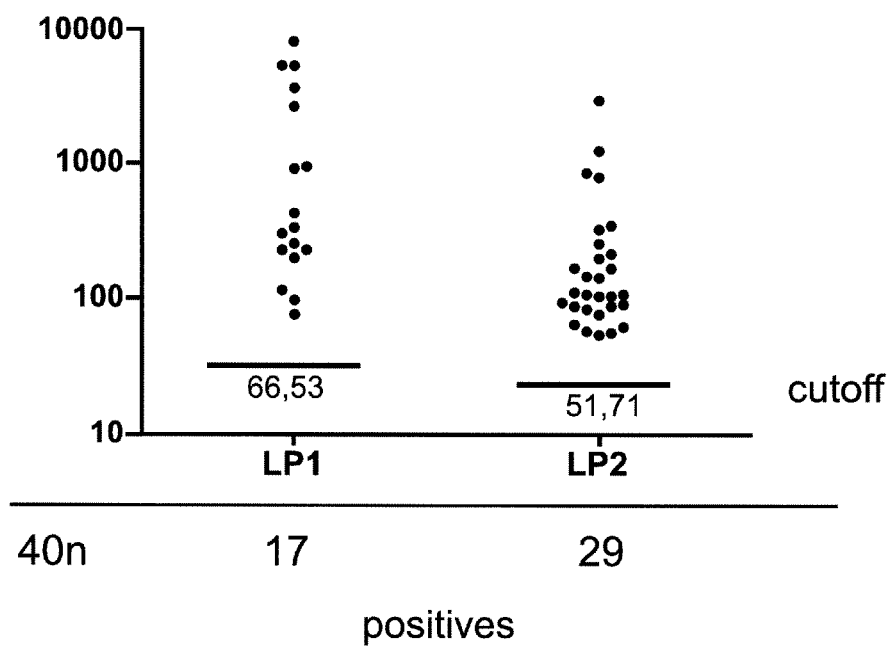
FIG. 10: Bioplex assay showing that some sera from the endemic region of Brazil can recognize the synthetic long peptides.

Results from this example demonstrate that Vir proteins are immunogenic in natural infections as some sera specifically recognized these long peptides (FIG. 10).

5.2 Vir Proteins are Antigenic and Capable of Eliciting Antibodies Reacting Against *P. vivax*-Infected Reticulocytes from Natural Infections.

To carry out more extensive analysis of Vir antigenicity, two antisera against these two peptides were generated in order to recognize Vir protein in natural isolates by immunofluorescence. Guinea pigs were immunized with these long peptides and anti-Lp1 and anti-Lp2 antisera were obtained. To validate different sub-cellular localization of Vir proteins in *P. vivax* wild isolates IFA assays with anti-Lp1 and anti-Lp2 were done.

The anti-Lp1 and anti-Lp2 antisera were generated by immunizing guinea pigs with peptides of SEQ ID NO 1 and SEQ ID NO 2. An aliquot of *P. vivax* infected red blood cells was washed once with incomplete RPMI and fixed as previously described (10). Fixed cells were permeabilized with 0.1% Triton X-100 in PBS and blocked for one hour in 3% PBS-BSA. Slides were incubated overnight with a guinea pig anti-Lp1 or anti-Lp2 antibodies. The reaction was developed using an anti-Guinea Pig IgG conjugated with Alexa Fluor 488 (Molecular Probes). Nuclei were stained for 10 minutes with DAPI (5 µl/ml diluted in PBS). Confocal microscopy was performed using a laser scanning confocal microscope (TCS-SP5; Leica Microsystems) and the images were processed using ImageJ image browser software.

Figure 11:
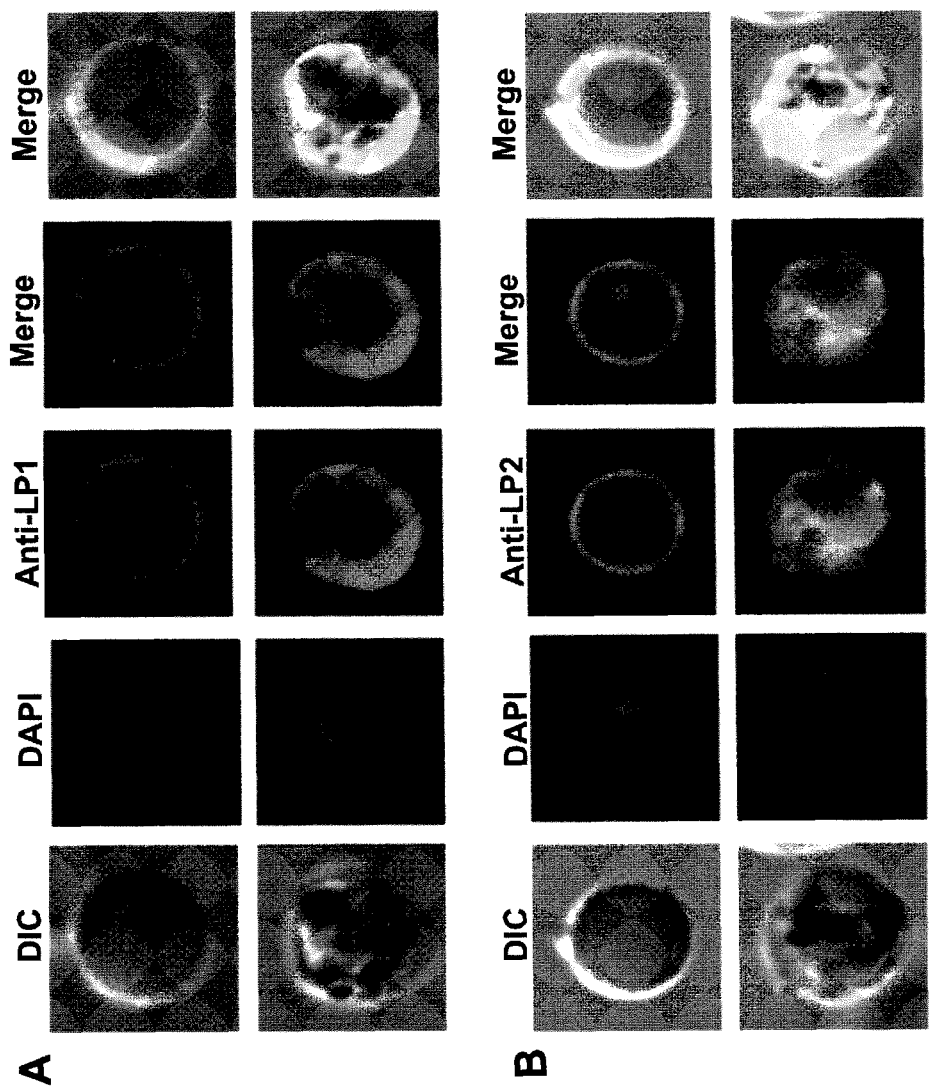
FIG. 11: Immunofluorescence assay showing that anti-Lp1 (A) and anti-Lp2 (B) can identify Vir proteins of *P. vivax* natural infections.

IFA assays of infected *P. vivax* patients (infection validated by PCR) showed a rim of fluorescence at the surface of the infected reticulocyte with a *P. vivax* ring stage (FIGS. 11A and 11B upper rows). In mature stages different stain patterns were found: close to the retyculocyte surface (FIG. 11A middle row) in the PVM and the surface of the infected retyculocyte (FIG. 11A down row) and inside the parasite body and in the infected retyculocyte cytosol (FIG. 11B down row).

Together this data show that Vir peptides are antigenic and capable of eliciting antibodies reacting against natural *P. vivax* isolates reinforcing their value as antigens for vaccine development.

Example 6

Preparation of Artificial Exosomes

Artificial exosomes containing peptides Lp1 and Lp2 were prepared with the following liposomal composition: 1,2-dioleoyl-sn-glycero-3-phosphocholine (DOPC), Cholesterol (CHOL), and 4-(p-maleimidophenyl)butyrylphosphatidylethanolamine (MBP-PE) in a molar ratio 79:20:1 and add 1 ug of the Vii peptides Lp1 and Lp2.

Lipids were dissolved and mixed in an organic solvent (chloroform:methanol, 2:1) to assure a homogenous mixture of lipids. Once lipids were mixed in the organic solvent, the solvent was removed to yield a lipid thin film on the sides of a round bottom flask by rotary evaporation. Remaining organic solvent traces were eliminated by drying under $N_2$ flow for 30 min. In order to ensure the complete removal of chloroform, films were left overnight in desiccators. The dry lipids were hydrated in PBS at 37° C.

Multilamellar liposomes were formed by 3 cycles of constant vortexing for 4 min on a vortex mixer followed by sonication in a bath for 4 min. Multilamellar liposomes were downsized to form uni- or oligolamellar vesicles by extrusion through 100-nm polycarbonate membranes in an extruder device (LiposoFast; Avestin, Ottawa, Canada). Liposome size was determined by dynamic light scattering using a Zetasizer NanoZS90 (Malvern Ltd, Malvern, UK).

Figure 12:
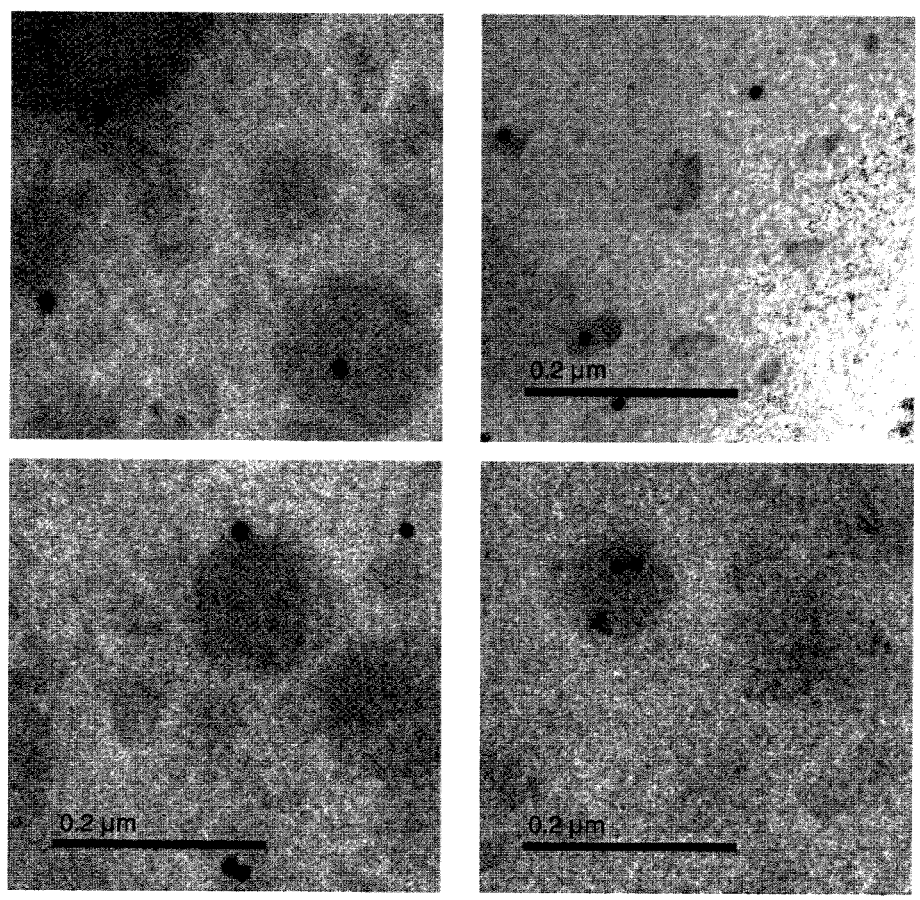
FIG. 12: Image of immunogold labeled artificial exosomes comprising Lp1 and Lp2 peptides as well as in their composition. The exosomes comprise 1,2-dioleoyl-sn-glycero-3-phosphocholine (DOPC), Cholesterol (CHOL), and 4-(p-maleimidophenyl)butyrylphosphatidylethanolamine (MBP-PE) in a molar ratio 79:20:1. Immunolabelling was performed with antibodies against LP1 and LP2 Vir peptides followed by Protein A-gold incubation Scale bar represent 200 nm.

The presence of Lp1 and Lp2 in the artificial exosomes was checked by immunolabelling with gold particles. Immunolabelling was performed with antibodies against LP1 and LP2 Vir peptides followed by Protein A-gold incubation. FIG. 12 reveals the presence of the peptides in the artificial exosomes.

This data demonstrates that exosomes containing malarial antigens can also be synthetically obtained.

REFERENCES

1. Schorey J S and Bhatnagar S. Exosome function: from tumor immunology to pathogen biology. *Traffic (Copenhagen, Denmark)* 2008; 9: 871-881.
2. Bhatnagar S, Shinagawa K, Castellino F J and Schorey J S. Exosomes released from macrophages infected with intracellular pathogens stimulate a proinflammatory response in vitro and in vivo. *Blood* 2007; 110: 3234-3244.
3. Viaud S, Ullrich E, Zitvogel L and Chaput N. Exosomes for the treatment of human malignancies. *Horm Metab Res* 2008; 40: 82-88.
4. Ribaut C, Berry A, Chevalley S et al., Concentration and purification by magnetic separation of the erythrocytic stages of all human *Plasmodium* species. *Malaria journal* 2008; 7: 45.

5. Stone K L and Williams K R. In The protein protocol handbook, ed. Walker J M, Totowa, N.J.: Humana Press Inc.; 1996.
6. Jurado J D, Rael E D, Lieb C S et al. Complement inactivating proteins and intraspecies venom variation in Crotalus oreganus helleri. *Toxicon* 2007; 49: 339-350.
7. Elias J E and Gygi S P. Target-decoy search strategy for increased confidence in large-scale protein identifications by mass spectrometry. *Nat Methods* 2007; 4: 207-214.
8. del Portillo H A, Fernandez-Becerra C, Bowman S et al. A superfamily of variant genes encoded in the subtelomeric region of *Plasmodium vivax*. *Nature* 2001; 410: 839-842.
9. Carlton J M, Adams J H, Silva J C et al. Comparative genomics of the neglected human malaria parasite *Plasmodium vivax*. *Nature* 2008; 455: 757-763.
10. Tonkin C J, van Dooren G G, Spurck T P et al. Localization of organellar proteins in *Plasmodium falciparum* using a novel set of transfection vectors and a new immunofluorescence fixation method. *Mol Biochem Parasitol* 2004; 137: 13-21.

The invention claimed is:

1. An isolated peptide comprising the amino acid sequence set forth as SEQ ID NO 1 or a sequence comprising at least 85% sequence identity to the amino acid sequence SEQ ID NO 1.

2. An isolated peptide comprising the amino acid sequence set forth as SEQ ID NO 2 or a sequence comprising at least 85% sequence identity to the amino acid sequence SEQ ID NO 2.

3. An artificial exosome comprising at least one *Plasmodium* sp. antigen in its interior or on its surface, wherein the *Plasmodium* sp. antigen is a peptide comprising the amino acid sequence set forth as SEQ ID NO 1 or 2, and/or a sequence comprising at least 85% sequence identity to the amino acid sequence set forth as SEQ ID NO 1 or 2.

4. A pharmaceutical composition comprising an exosome comprising at least one *Plasmodium* sp. antigen in its interior or on its surface, wherein the *Plasmodium* sp. antigen is a peptide comprising the amino acid sequence set forth as SEQ

SEQUENCE LISTING

```
<160> NUMBER OF SEQ ID NOS: 2

<210> SEQ ID NO 1
<211> LENGTH: 74
<212> TYPE: PRT
<213> ORGANISM: Plasmodium vivax

<400> SEQUENCE: 1

Val Lys Glu Leu Cys Lys Lys Leu Val Arg Asn Leu Lys Lys Ile Ser
1               5                   10                  15

Cys Ile Tyr Leu Asn Tyr Trp Leu Tyr Asp Gln Ile Lys Glu Arg Lys
            20                  25                  30

Asp Leu His Asp Tyr Phe Lys Asn Tyr Asp Thr Ile Lys Cys Cys Glu
        35                  40                  45

Lys Tyr Cys Thr Tyr Val Thr Tyr Ile Lys Ser Leu Tyr Glu Tyr Asp
    50                  55                  60

Pro Lys Asp Leu Leu Ser Lys Leu Asp Cys
65                  70

<210> SEQ ID NO 2
<211> LENGTH: 112
<212> TYPE: PRT
<213> ORGANISM: Plasmodium vivax

<400> SEQUENCE: 2

Ile Ala Asp Ser Pro Gly Thr Leu Gly Thr Val His Glu Glu Leu Asp
1               5                   10                  15

Ser Asn Phe Phe Arg Asn Ile Ile Met Val Val Gly Val Met Met Thr
            20                  25                  30

Phe Phe Phe Leu Tyr Lys Phe Thr Pro Val Gly Ala Phe Phe Arg Gly
        35                  40                  45

Gly Arg Gly Arg Val His Arg Ile Pro Arg Ser Phe His Gly Gln Phe
    50                  55                  60

Pro Gly Lys Arg Lys Gly Lys Ile Phe Glu His Asn Tyr Tyr Glu Glu
65                  70                  75                  80

Tyr Glu Lys Glu Leu Ala Met Tyr Gly Ser Glu Phe Leu Asp Ser Gln
            85                  90                  95

Met Asp Arg Tyr Tyr Leu Asn Tyr Gln Pro Asp Gln Asp Ser Tyr Tyr
            100                 105                 110
```

ID NO 1 or 2, and/or a sequence comprising at least 85% sequence identity to the amino acid sequence set forth as SEQ ID NO 1 or 2.

* * * * *